United States Patent [19]

Ploss

[11] Patent Number: 4,560,702
[45] Date of Patent: Dec. 24, 1985

[54] PESTICIDAL $C_6$–$C_{25}$-MERCAPTO-ORGANOTIN COMPOUNDS

[75] Inventor: Hartmut Ploss, Hamburg, Fed. Rep. of Germany

[73] Assignee: Norddeutsche Affinerie AG, Hamburg, Fed. Rep. of Germany

[21] Appl. No.: 505,058

[22] Filed: Jun. 16, 1983

[30] Foreign Application Priority Data

Jun. 23, 1982 [DE] Fed. Rep. of Germany ....... 3223335

[51] Int. Cl.⁴ ............................................. A01N 55/04
[52] U.S. Cl. ...................................... 514/493; 556/88
[58] Field of Search ......................... 424/288; 514/493

[56] References Cited

U.S. PATENT DOCUMENTS

| | | | |
|---|---|---|---|
| 3,247,050 | 4/1966 | Leebrick | 424/288 |
| 3,264,177 | 8/1966 | Kenaga | 424/288 |
| 3,288,669 | 11/1966 | Hechenbleikner | 424/288 |
| 3,463,644 | 8/1969 | Hechenbleikner et al. | 424/288 |
| 3,892,863 | 7/1975 | Gitlitz et al. | 424/288 |
| 3,923,998 | 12/1975 | Gitlitz | 424/288 |

FOREIGN PATENT DOCUMENTS 55-17318 2/1980 Japan .

*Primary Examiner*—Allen J. Robinson
*Attorney, Agent, or Firm*—Karl F. Ross; Herbert Dubno

[57] ABSTRACT

The invention relates to novel organotin mercaptides and their preparation. The novel organotin mercaptides are particularly suitable as pesticides. In order to increase the biological activity and to ensure that there will be no damage to plants, a sulfur-containing organotin compound which constitutes the active ingredient of a pesticide consists of tricyclohexyltin alkanyl mercaptide or tricyclohexyltin alkenyl mercaptide. The alkanyl chain or alkenyl chain contains 6 to 25 carbon atoms and may be substituted and/or branched. The substituent may consist of halogen or the nitro group. The active ingredient of the pesticide consists particularly of tricyclohexyltin octyl mercaptide, tricyclohexyltin-2,2-dipropylheptyl mercaptide, tricyclohexyltindodecyl mercaptide, or tricyclohexyltin undecenyl mercaptide. The agent is used for the control of acarina and insects, particularly mites and ticks.

8 Claims, No Drawings

PESTICIDAL $C_6$–$C_{25}$-MERCAPTO-ORGANOTIN COMPOUNDS

FIELD OF THE INVENTION

The present invention relates to new, sulfur-containing organotin compounds, their preparation and a method of use of the new compounds as pesticides.

BACKGROUND OF THE INVENTION

Organotin compounds are known for their high degree of activity against microorganisms, such as fungi, bacteria and algae, and against insects, mites, molluscs and other small living beings.

It is of special significance that these compounds differ from other biocides, which contain heavy metals, such as copper or mercury, in organic or inorganic compounds, in that the tin compounds decompose to nontoxic inorganic tin compounds by physical, chemical and biochemical processes.

Another advantage afforded by the organotin compounds is their activity against pests which may be resistant to conventional biocides.

German Pat. No. 950,970 discloses for the control of microorganisms, such as fungi, bacteria and Protozoa, a pesticide containing an active ingredient consisting of an organotin compound of the formula $R_3SnX$, wherein R represents is an organic moiety and $R_3$ represents three such moieties which may be the same or different.

It is apparent from the specification that R can be methyl, ethyl, propyl, butyl or phenyl. In the formula $R_3SnX$, X can represent OH, O-acyl, O-alkyl, SH, S-alkyl, S-aryl, $SO_2$-alkyl, $SO_2$-aryl, $NHSO_2$-alkyl or $NHSO_2$-aryl. The respective alkyl and aryl groups may be substituted or unsubstituted. The document does not, however, contain any information regarding the nature of the triorganotin compounds in case an alkyl residue or aryl residue is linked by a sulfur atom to the tin atom.

It is also known to change the toxicity profile by a controlled selection of the organic groups attached to the tin atom. For instance, the replacement of butyl groups by cyclohexyl groups results in tricylohexyltin compounds which are highly effective and hardly detrimental to plants. It is known that tricyclohexyltin hydroxide (Cyhexatin) (Laid-open German Application No. 15 42 863) and tricyclohexyltin triazole (AZOcyclotin) have a prolonged nonsystemic activity against mobile spider mite stages, even against pesticide-resistant species.

By the attachment of suitable biocidal groups to the fourth valency bond of the tin atom of these tricyclohexyl tin compounds the latter can be converted to compounds having a synergistically improved activity. For instance, Laid-open German Application No. 15 42 863 describes arachnicides which contain tricyclohexyl tin compounds in which the fourth valency bond of the tin atom is saturated by an alkyl or alkylene residue, such as lauryl tricyclohexyltin or oleyl tricyclohexyltin. An attachment to the molecule may be effected via a sulfur atom which has a free valency bond that is saturated by an alkanoyl residue or benzoyl residue, such as lauroyl thiotricyclohexyltin. An attachment of a thioalkyl or thioalkylene residue to the fourth residual valency bond of the tin atom is not apparent from that document.

The biological activity of all these compounds is inadequate for the control of certain pests, particularly of mites.

In accordance with a proposal disclosed in Laid-open German Application No. 20 59 279, sulfur-containing trihexyltin compounds in which the sulfur atom is attached to tin and to a lower alkyl group are described, inter alia. That printed publication does not teach the use of a lower alkyl group other than the propyl group.

Whereas the previously known organotin compounds are useful insecticides, they have only a restricted field of application because they result in phytotoxic damage to numerous plants.

OBJECTS OF THE INVENTION

It is an object of the invention to provide a pesticide which is entirely innocuous to plants and which has an increased biological activity, particularly against spider mites.

Another object of my invention is to provide an organotin compound with improved arachanicidal activity and without the drawbacks of other pesticides, which is environmentally safe and yet effective, and which has advantages where the pest to be attacked has grown resistant to other pesticides.

Still another object of the invention is to provide a plant-site treatment method for the control of pests, particularly the spider mite, which has less of a phytotoxic effect and a greater pesticidal effect than earlier methods.

It is also an object of this invention to provide a method of making the new compounds.

These objects are accomplished in accordance with the invention by the provision of novel sulfur-containing tricyclohexyltin compounds. The novel sulfur-containing tricyclohexyltin compounds have the formula $(C_6H_{11})_3Sn$—SR wherein R is a branched or unbranched saturated or mono, di or polyunsaturated $C_6$–$C_{25}$ aliphatic chain, namely an alkanyl chain or alkenyl chain which has 6 to 25 carbon atoms and which can be substituted, e.g., with halo (preferably chloro) or nitro. Specifically, the residue R is a higher alkanyl chain having 8 to 15 carbon atoms. That chain may be substituted and/or branched, if desired. The subsituents may be more than one in number and located anywhere on the chain.

In accordance with the invention, new compounds of the above-mentioned type contain, e.g., the dodecyl, dipropylheptyl, undecenyl or octyl residue, which is attached to the sulfur.

It has also been found that the tricyclohexyltin compounds in which a higher aliphatic residue of the invention is attached to the tin-sulfur bond have an extremely high pesticidal activity, particularly against mites, ticks and insects. It is particularly remarkable that in spite of the excellent adhesion of the agent to parts of the treated plants, the latter are not adversely affected by an excessively high phytotoxicity.

In the pesticide of the invention, the alkanyl or alkenyl residue which is attached to the sulfur atom has preferably more than 6 carbon atoms and may contain up to 25 carbon atoms. It most advantageously contains 8 to 15 carbon atoms and particularly 12 carbon atoms. The effectiveness of the alkanyl or alkenyl residue may be varied by the number and kinds of the substituents used.

It has proved favorable to provide a branched alkyl chain in the pesticide according to the invention. Such a suitable compound is, e.g., tricyclohexyltin-2, 2-dipropyl-heptyl mercaptide. Particularly preferred organotin compounds in accordance with the invention are tricyclohexyltin octyl mercaptide, tricyclohexyltin undecenyl mercaptide, and tricyclohexyl tin dodecyl mercaptide.

The pesticides of the invention which contain sulfur-containing organotin compounds are particularly active against mites, ticks and insects. They are especially active against sensitive and resistant Acarina, such as Panonychus spp., Tetranychus spp., *Eotetranychus carpini, Phyllocoptruta oleivora;* also against Ixoidea; against insects, such as *Aonidiella aurantii, Trialeurodes vaporariorum, Dystercus cingulatus, Spodoptera littoralis, Adoxophyes reticulana, Leptinotarsa decemlineata, Laspeyresia pomonella, Heliothis virescens,* including their egg stages, particularly the winter eggs.

The pesticide of the invention may be put up for use in a conventional form, such as a spray powder, emulsion, suspension, granulate, water-dispersible particulate, and in such cases can contain in addition to the active ingredient or combination of active ingredients, conventional adjuvants, such as inert substances, wetting agents, dispersing agents and emulsifying agents.

The pesticide composition of the invention contains the active ingredient, namely one or more of the new compounds, in a proportion of 12 to 80%, preferably of 25 to 50% by weight.

The pesticide of the invention is used in different proportions for various applications. For instance, for the treatment of plants in order to control pests on the plants, the active component is suitably employed by spraying the plant site with about 0.1 to 2.0 kg/ha.

In the treatment of animals for the control of ectoparasites, the animal is suitably immersed into or sprayed with a solution which contains the active compound in an amount of 100 to 1000 ppm.

If the pesticide of the invention is to be used to control other pests at the same time and at the same location, corresponding other substances may be added to the pesticide. Such other compounds can include conventional agents for modifying plant growth or herbicides for the control of undesired vegetation.

The new sulfur-containing tricyclohexyltin compounds proposed by the invention are produced by a process in which tricyclohexyltin halide containing an alkyl mercaptan or an alkylene mercaptan having 6 to 25, preferably 8 to 15 carbon atoms in the chain, which may be branched and/or substituted, e.g., by halogen or a nitro group, is reacted in a non-reactive liquid medium with stirring and in the presence of an alkaline condensing agent, the reaction product is dissolved in an organic solvent, and the organic solvent is separated from the purified and dried solution of the mercaptide.

Tricyclohexyltin chloride is suitably reacted with octyl mercaptan, undecenyl mercaptan, 2,2-dipropylheptyl mercaptan or doecyl mercaptan.

The reaction is effected with strong stirring and under reflux in a non-reactive liquid medium, such as water, acetone, benzene or mixtures thereof, in the presence of an alkaline condensing agent. The reaction temperature rises to 60° C. Alkali hydroxide and particularly potassium hydroxide is suitably employed. In a reaction effected in benzene, triethylamine is used as an alkaline condensing agent.

The reaction product, which is formed as an oily phase, is dissolved in an organic solvent and the resulting alkali halide is removed by shaking with water of the organic phase. The organic phase is thoroughly dried and the product is recovered by driving off the organic solvent under subatmospheric pressure.

SPECIFIC EXAMPLES

The invention will be explained more fully with reference to the following Examples.

Examples 1 to 5 explain the preparation of the active ingredient of the pesticide according to the invention. Example 6 relates to the preparation of the ingredient according to the invention in the form of an emulsion.

EXAMPLE 1

Preparation of Tricyclohexyltin Dodecyl-Mercaptide
Tricyclohexyl-Sn—S—$(CH_2)_{11}$—$CH_3$ 40.4 grams tricyclohexyltin chloride (0.1 mole) are suspended in 30 ml acetone and 130 ml water. 21 grams dodecyl mercaptan (0.1 mole) are then added with strong stirring within 2 hours. Thereafter a solution of 5.6 grams potassium hydroxide in 100 ml water are added and the stirring of the suspension is continued for 30 minutes. An oily product is formed in the suspension and is dissolved in ether and shaken out with water. The aqueous layer contains 3.4 grams ionogenic chlorine. The ethereal layer is dried over magnesium sulfate and evaporated in a vacuum. The resulting colorless and odorless liquid had a decomposition temperature of 265° C. under a pressure of 270 mm mercury.

Analysis in % by weight: Calculated for $C_{30}H_{58}SSn$: C=63.3, H=10.3, S=5.6. Found: C=63.7, H=10.5, S=5.7.

EXAMPLE 2

Preparation of Tricyclohexyltin-2, 2-dipropylheptyl Mercaptide
Tricyclohexyl-Sn—S—$(CH_2)_5$—$C(C_3H_7)_2$—$CH_3$ In a repetition of Example 1, 2,2-dipropylheptyl mercaptan was used instead of dodecyl mercaptan. A colorless and odorless liquid was obtained, which had a decomposition temperature of 215° C. under a pressure of 270 mm mercury.

Analysis in % by weight: Calculated for $C_{31}H_{60}SSn$: C=63.8, H=10.4, S=5.5. Found: C=64.0, H=10.5, S=5.6.

EXAMPLE 3

Preparation of Tricyclohexyltin Undecenyl Mercaptide
Tricyclohexyl-Sn—S—$(CH_2)_6$—CH=CH—$C_3H_7$ In a repetition of Example 1, undecenyl mercaptan, which is an unsaturated higher thiohydrocarbon, was used instead of the dodecyl mercaptan. The resulting colorless, highly viscous liquid had a decomposition temperature of 190° C. under a pressure of 270 mm mercury.

Analysis in % by weight: Calculated for $C_{29}H_{54}SSn$: C=62.9, H=9.8, S=5.8. Found: C=62.7, H=9.7, S=5.8.

EXAMPLE 4

Preparation of Tricyclohexyltin Octyl Mercaptide
$(C_6H_{11})_3-Sn-S-(CH_2)_7-CH_3$ In a repetition of Example 1, the n-octyl mercaptan was used instead of the dodecyl mercaptan. The resulting yellowish and odorless liquid had a decomposition temperature of 230° C. under a pressure of 270 mm mercury.

Analysis in % by weight: Calculated for $C_{26}H_{50}SSn$: C=60.8, H=9.8, S=6.2. Found: C=60.4, H=9.7, S=6.2.

EXAMPLE 5

Preparation of Tricyclohexyltin Hexadecanyl Mercaptide $(C_6H_{11})_3-Sn-S-(CH_2)_{15}-CH_3$ In a repetition of Example 1, the hexadecanyl mercaptan was used instead of the dodecyl mercaptan. The white crystalline product thus obtained had a melting point of 29° C.

Analysis in % by weight: Calculated for $C_{34}H_{66}SSn$: C=65.3; H=10.6, S=5.1. Found: C=65.0, H=10.3, S=5.2.

EXAMPLE 6

Emulsion concentrates containing the active agent proposed by the invention were prepared in known manner in that the active agent was stirred into a xylene-emulsifier mixture. The emulsifier consisted of 40 wt, % tributyl phenol polyglycol ether and 60 wt. % calcium alkyl aryl sulfonate.

Emulsion concentrates consisting of
25 wt. % active agent
50 wt. % xylene
25 wt. % emulsifier
were made with the following active ingredients:
Tricyclohexyltin dodecyl mercaptide
Tricyclohexyltin dipropyl heptyl mercaptide
Tricyclohexyltin undecenyl mercaptide
Tricyclohexyltin octyl mercaptide
Tricyclohexyltin hexadecanyl mercaptide From the following Examples 7 to 10, the superior biological activity of the pesticide of the invention will be apparent. The control substances employed consisted of Cyhexatin (tricyclohexyltin hydroxide) as a commercially available akaricide containing an organotin compound, and tricyclohexyltin pentyl mercaptide, which is tricyclohexyl-organotin compound having a tin-sulfur bond and a lower alkyl group attached to the sulfur atom, in accordance with Laid-open German Application No. 20 59 279.

EXAMPLE 7

Controlled species: *Tetranychus urticae*, red spider mite.

Bean plants having two leaves were sprayed with an acetone solution of the test compound of known concentration. After that treatment, two leaf discs 3 centimeters in diameter are invested with 10 viable mites each and the leaf discs were subjected on a moist foam rubber pad to an atmosphere having a relative humidity of 60% at 25° C. Untreated leaf discs and leaf discs treated only with acetone served as control discs. The test was carried out for 3 days. This resulted in a reduction of viable mites in percent compared with controls.

The results are stated in Table 1. The activity of the active agent is stated in percent and its dosage is stated in grams of active ingredient (a.i.) per $cm^2$.

TABLE 1

| | Activity in % | |
|---|---|---|
| Dosage ($10^{-x}$ g a.i./$cm^2$) | x = 7 | x = 8 |
| Composition of Example 1 (tricyclohexyltin dodecyl mercaptide) | 100 | 100 |
| Composition of Example 4 (tricyclohexyltin octyl mercaptide) | 100 | not tested |
| cyhexatin (tricyclohexyltin hydroxide) | 59 | 18 |
| $(C_6H_{11})_3-Sn-S-(CH_2)_4-CH_3$ | 40 | 23 |
| Untreated specimen mortality 2% | | |

EXAMPLE 8

Controlled species: *Tetranychus urticae*, spotted spider mites of sensitive and Phosalon-resistant strains.

Method: A mixed population of the spider mites was applied to bush beans. The specimens were prepared as in Example 7 and were sprayed with the preparation containing the test compound (25% active ingredient, 50% xylene, 25% emulsifier; see Example 6) and then kept in an atmosphere having a relative humidity of 60% at 25° C. for 7 days.

The results are stated in the following Table 2 as the percentage of the reduction of viable mites in percent compared with controls.

TABLE 2

| | Activity in % | | |
|---|---|---|---|
| Dosage in % of active ingredient | 0.003 | 0.001 | 0.0003 |
| Sensitive strain | | | |
| Compound of Example 1 | 98 | 74 | |
| Compound of Example 4 | 100 | 73 | |
| Cyhexatin | 97 | 8 | |
| Tricyclohexyltin pentyl mercaptide | 32 | 32 | |
| Phosalon-resistant strain | | | |
| Compound of Example 1 | 99 | 95 | 65 |
| Compound of Example 4 | 98 | 78 | not tested |
| Cyhexatin | 98 | 83 | 10 |
| Tricyclohexyltin pentyl mercaptide | 30 | 10 | not tested |

EXAMPLE 9

Controlled species: *Aonichiella aurantii*, Californian red scales.

Method: 50 to 100 larvae of the first stage were applied to potato tubers. One day after the infestation the tubers were sprayed with an acetone solution containing the active ingredient in a known concentration. The treated potato tubers were placed into plastic cups and were stored in an atmosphere having a relative humidity of 60% at 25° for 21 days. The control specimens consisted of tubers treated with pure acetone.

The results are expressed in Table 3 as the reduction of the quantity of viable larvae in percent compared with the specimen not treated with active ingredient.

TABLE 3

| | Activity in % | |
|---|---|---|
| Dosage ($10^{-x}$ g a.i./$cm^2$) | x = 6 | x = 7 |
| Compound of Example 1 | 100 | 18 |
| Compound of Example 4 | 100 | 9 |
| Cyhexatin | 19 | 0 |
| Tricyclohexyltin pentyl mercaptide | 24 | 0 |
| Specimen not treated with active ingredient: | | |
| Mortality 4% | | |

EXAMPLE 10

Controlled species: *Adoxophyes orana*, summer fruit tortrix moth.

10 first-stage larvae were applied to leaf discs 26 mm in diameter of apple trees. The discs were then sprayed with an acetone solution containing the active ingredient in a known concentration and were kept on moist filter paper in small plastic cups in an atmosphere having a relative humidity of 60% at 25° C. for 4 days.

The control material consisted of specimens treated only with acetone.

The result is stated in Table 4 as the reduction in percent of the quantity of surviving larvae compared to specimens not treated with an active ingredient.

TABLE 4

| Dosage ($10^{-x}$g.a.i./cm$^2$) | Activity in % | |
|---|---|---|
| | x = 6 | x = 7 |
| Compound of Example 1 | 100 | 90 |
| Compound of Example 4 | 100 | 20 |
| Cyhexatin | 8 | 0 |
| Tricyclohexyltin pentyl mercaptide | 33 | 14 |
| Specimen not treated with active ingredient: Mortality 3% | | |

I claim:

1. A pesticide for application to a plant site against mites or ticks containing an effective amount of a compound of the formula $$(C_6H_{11})_3Sn-SR$$

wherein R is a branched or unbranched $C_8$ to $C_{25}$ alkanyl chain or $C_8$ to $C_{25}$ alkenyl chain, said alkanyl or alkenyl chain being unsubstituted or substituted by halo or nitro, along with a pesticidally acceptable carrier.

2. The pesticide defined in claim 1 which contains an effective amount of a compound of the formula $$(C_6H_{11})_3Sn-SR$$

wherein R is a branched or unbranched $C_8$ to $C_{15}$ alkanyl chain or $C_8$ to $C_{15}$ alkenyl chain.

3. The pesticide defined in claim 2 wherein said compound is selected from the group which consists of: tricyclohexyltin dodecyl mercaptide; tricyclohexyltin dipropylheptyl mercaptide; tricyclohexyltin undecenyl mercaptide; and tricyclohexyltin octyl mercaptide.

4. The pesticide defined in claim 2 which contains an effective amount of a compound of the formula $$(C_6H_{11})_3Sn-SR$$

wherein R is a branched or unbranched $C_8$ to $C_{15}$ alkenyl chain.

5. A method of controlling mites or ticks at a plant site which comprises the step of applying to said site an insecticidally effective amount of a composition containing at least one compound of the formula:

$$(C_6H_{11})_3Sn-SR$$

wherein R is a branched or unbranched $C_8$ to $C_{25}$ alkanyl chain or $C_8$ to $C_{25}$ alkenyl chain which may be substituted by halo or nitro, along with a pesticidally acceptable carrier.

6. The method defined in claim 5 wherein the composition contains an effective amount of a compound of the formula:

$$(C_6H_{11})_3Sn-SR$$

wherein R is a branched or unbranched $C_8$ to $C_{15}$ alkanyl chain or $C_8$ to $C_{15}$ alkenyl chain.

7. The method defined in claim 5 wherein the composition contains a compound which is selected from the group which consists of tricyclohexyltin dipropylheptyl, undecenyl, octyl and dodecyl mercaptides.

8. The method defined in claim 5 wherein the composition contains an effective amount of a compound of the formula $$(C_6H_{11})_3Sn-SR$$

wherein R is a branched or unbranched $C_8$ to $C_{15}$ alkenyl chain.

* * * * *